United States Patent [19]

Bel et al.

[11] 4,427,014

[45] Jan. 24, 1984

[54] BIOPSY FORCEPS

[75] Inventors: Roger P. Bel, Massy; Michel M. Regnier, Ris-Orangis; Martial E. Hascoët, Paris, all of France

[73] Assignee: Metallisations et Traitements Optiques M.T.O., Massy, France

[21] Appl. No.: 274,514

[22] Filed: Jun. 17, 1981

[30] Foreign Application Priority Data

May 6, 1981 [FR] France ................... 81 09035

[51] Int. Cl.³ ........................... A61B 10/00
[52] U.S. Cl. ........................ 128/751; 128/305
[58] Field of Search ............... 128/4, 92 EA, 303 A, 128/303.14, 303.15, 303.17, 305, 319, 321, 325, 346, 354, 642, 749, 751, 757

[56] References Cited

U.S. PATENT DOCUMENTS

| | | | |
|---|---|---|---|
| 2,214,985 | 9/1940 | Bachmann | 128/321 |
| 2,670,519 | 3/1954 | Recklitis | 128/321 X |
| 3,404,677 | 8/1968 | Springer | 128/751 |
| 3,967,625 | 7/1976 | Yoon | 128/303 A |
| 4,005,714 | 2/1977 | Hiltebrandt | 128/303.17 |
| 4,054,143 | 8/1977 | Bauer | 128/303.17 |
| 4,080,961 | 3/1978 | Eaton | 128/642 |
| 4,200,111 | 4/1980 | Harris | 128/751 |
| 4,257,420 | 3/1981 | Terayama | 128/303 A |

*Primary Examiner*—Edward M. Coven
*Assistant Examiner*—Christine A. Fukushima
*Attorney, Agent, or Firm*—Finnegan, Henderson, Farabow, Garrett & Dunner

[57] ABSTRACT

Biopsy forceps for use with a contact endoscope having a body terminating in a distal end comprising a hollow outer tube open at both ends, a hollow inner tube located coaxially within the outer tube, the inner tube being open at its rear end and terminating at its front end in at least one pair of diametrically opposed tongues that extend outwardly beyond the front end of the outer tube and in a direction substantially parallel to the longitudinal axis of the tubes and then bend inwardly at their far end at right angles to the longitudinal axis terminating in a series of teeth to form forceps jaws, the jaws being biased in a direction away from the axis, whereby movement of the tubes in one direction relative to one another causes the tongues of the jaws to slide into the outer tube and the forceps jaws to close and movement in the opposite direction causes the jaws to open, and a control device for axially moving one of the tubes relative to the other to activate the jaws, whereby the endoscope can be inserted all the way through the forceps from its rear end so that the distal end of the endoscope lies against the forceps jaws.

4 Claims, 6 Drawing Figures

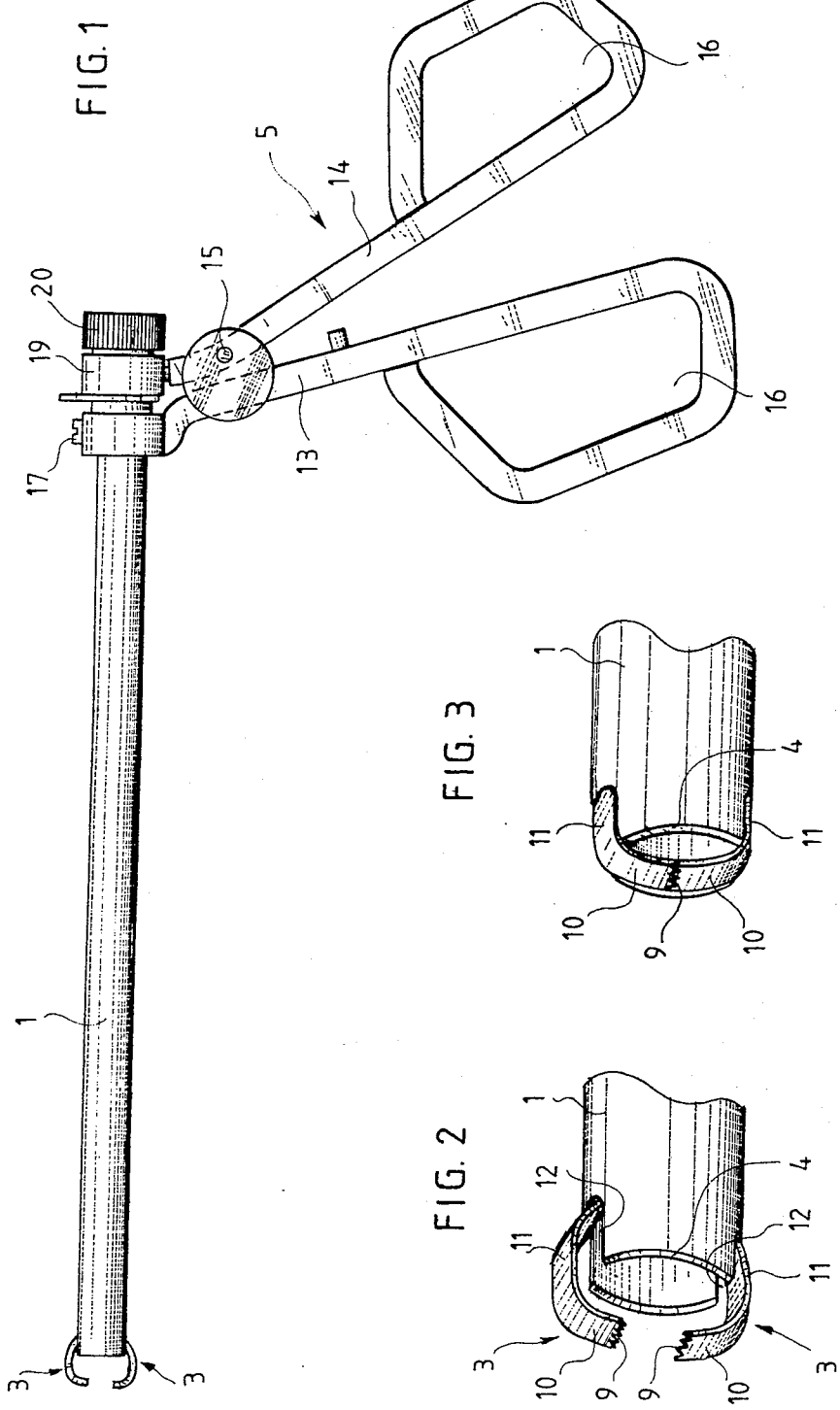

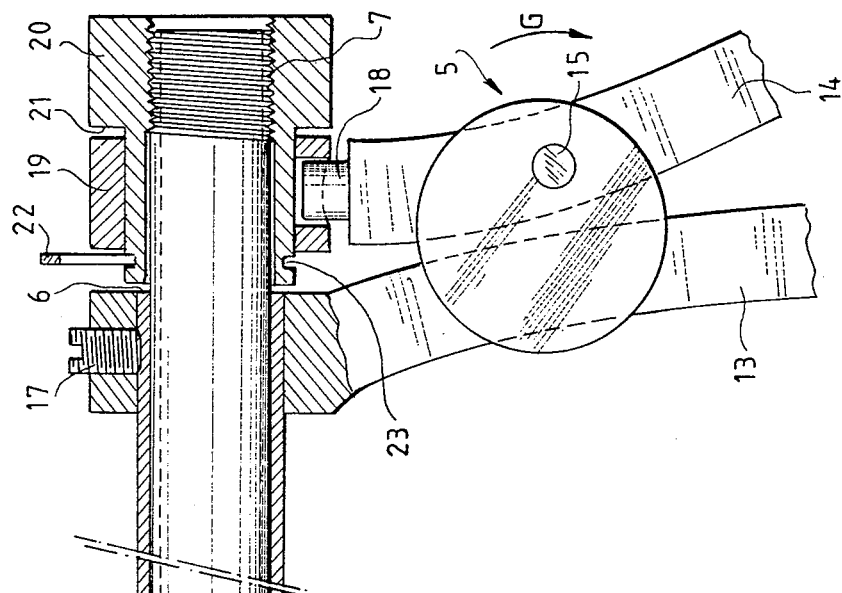
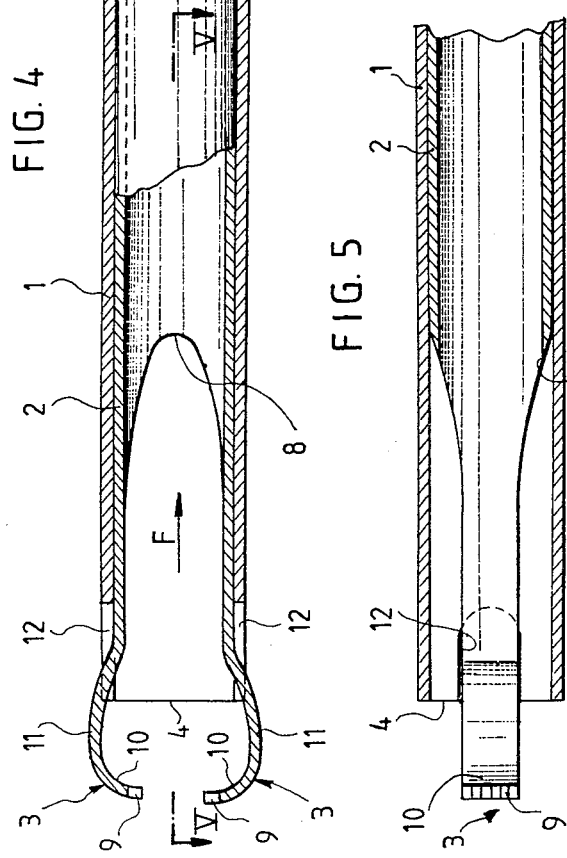
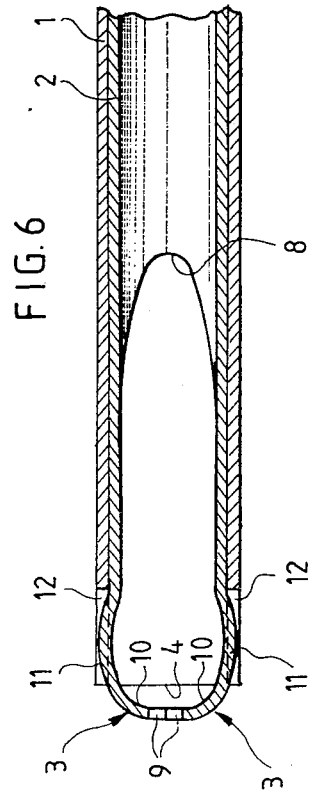

BIOPSY FORCEPS

The present invention relates to biopsy forceps the body of which comprises an outer tube, an inner tube fitted into the outer tube with which it extends coaxially, jaws projecting from the front end of the outer tube, these jaws being movable between an open position in which they are moved away from the longitudinal axis of the two tubes and a closed position in which they come together along this axis, and control means for axially moving one of the two tubes and for simultaneously actuating the jaws.

Biopsy forceps of this type have been perfected by applicant for taking samples of cellular tissues inside cavities of human or animal bodies. Their originality resides in their tubular structure which allows them to be fitted over the body of a contact endoscope by means of which the practitioner may observe the internal wall of the cavity and visually select the fragment of tissue to be taken. For a detailed description of these biopsy forceps, reference may be made to French Patent Application No. 80 07480 filed Apr. 2, 1980 by applicants herein and published Oct. 9, 1981.

These forceps do not however give entire satisfaction. Their jaws may in fact be closed over the selected fragment of tissue only if the contact endoscope has been moved a sufficient distance away therefrom. Now, when the distal end of the endoscope is no longer in the vicinity of the free end of the jaws, the practitioner can no longer correctly see the tissue in front of them and risks taking a fragment which is not the one he had selected at the outset.

Furthermore, the jaws of these forceps end in a tapered portion which risks causing internal lesions when they are introduced into the cavity containing the tissue a sample of which is to be taken.

The present invention proposes remedying these drawbacks and, for this, it provides a biopsy forceps which is characterized in that the jaws are carried by the front end of the inner tube and extend in the direction of the front end of the outer tube while moving slightly apart from each other, these jaws ending in teeth formed at the end of a part bent substantially at right angles in the direction of the longitudinal axis of the two tubes and being actuated by the outer tube during the relative movement of the two tubes.

These forceps are formed from a much smaller number of parts than the biopsy forceps of the above-mentioned type and may thus be produced simply and for a lower cost price.

Moreover, since the jaws are terminated by a part bent substantially at right angles, the distal end of the endoscope may now remain in contact with them when they are closed. The practitioner can thus see the fragment of tissue while taking the sample and no longer risks taking a fragment other than the one he had selected when the jaws were open.

Moreover, the jaws are free of tapered projecting parts, which removes the risks of accidental injuries during the introduction thereof into the cavity.

According to a preferred embodiment of the forceps of the invention, the jaws are formed by two diametrically opposite tongues extending the front end of the inner tube.

These two tongues give to the forceps a structure which is obviously very simple.

Advantageously, each tongue comprises, between its bent part and its connection with the inner tube, a swelling cooperating with a longitudinal notch formed at the front end of the outer tube, this swelling projecting outside the notch when the jaws are open and extending into the notch when the jaws are closed.

Thus the jaws do not project from the lateral wall of the outer tube when they are closed, which further reduces the risk of injury.

One embodiment of the present invention will be described hereafter by way of example, which is in no wise limiting, with reference to the accompanying drawings in which:

FIG. 1 is a side view of biopsy forceps in accordance with the invention;

FIG. 2 is an enlarged perspective view of the front end of the outer tube of the forceps, the jaws thereof being shown open;

FIG. 3 is a view similar to FIG. 2 but in which the jaws are shown closed;

FIG. 4 is a partial enlarged view in axial section of the forceps shown in FIG. 1;

FIG. 5 is a sectional view along line V—V of FIG. 4; and

FIG. 6 is an axial sectional view of the front end of the forceps shown in FIG. 4 but in which the jaws are shown closed.

The biopsy forceps which can be seen in the drawings comprise an outer tube 1, an inner tube 2 fitted into the outer tube with which it extends coaxially, two jaws 3 projecting from the front end 4 of the outer tube, and control means 5 for axially moving one of the two tubes and for simultaneously actuating the jaws.

In the example shown, the control means 5 are provided so as to move the inner tube axially within the outer tube. But is is evident that they could move the outer tube on the inner tube.

The inner tube has an outer diameter which is slightly smaller than the inner diameter of the outer tube. It extends beyond the rear end 6 thereof and terminates in a threaded part 7 the role of which will become clear hereafter.

The jaws are movable between an open position (shown in FIGS. 1, 2 and 4) in which they are moved away from the longitudinal axis of the two tubes and a closed position (shown in FIGS. 3 and 6) in which they come together along this axis. They are carried by the front end 8 of the inner tube and extend towards the front end 4 of the outer tube while moving slightly away from each other. Thus, with their divergent shape, the outer tube will ensure closing thereof during retraction of the inner tube and will allow them to open by themselves under the effect of their elasticity when the inner tube is brought back to its initial position.

In the embodiment shown in the drawings, the jaws are formed by two diametrically opposed tongues extending the front end 8 of the inner tube. They end in teeth 9 formed at the end of a part 10 bent substantially at right angles in the direction of the longitudinal axis of tubes 1 and 2. They each comprise further, between their bent part 10 and their connection with the inner tube, a swelling 11 cooperating with a longitudinal notch 12 formed at the front end 4 of the outer tube. As is shown in FIGS. 4 and 6, the swellings 11 are shaped so as to project outside notches 12 when the jaws are open and to extend in the notches when these latter are closed.

As for the control means 5, they are formed by two gripping arms 13 and 14 hinged to one another about a pin 15 and the lower ends of which end in two loops 16 intended to receive respectively the thumb and the forefinger of the person using the forceps.

Referring more especially to FIG. 4, it will be noted that the upper end of arm 13 is fitted over the outer tube 1 and is secured against motion thereon by means of a grub screw 17. It will also be noted that the upper end of arm 14 ends in a stud 18 inserted into a bore formed in a socket 19. This latter, which is fitted over a sleeve 20 screwed onto the threaded part 7 of the inner tube, is secured against motion between a shoulder 21 of the sleeve and a resilient removable ring 22 held in a groove 23 formed therein.

The special configuraion of the upper ends of the two gripping arms and of the parts retaining them on the two tubes allows easy and rapid assembly and disassembly of the forceps, with a view to cleaning same.

In order to disassemble the forceps, it is in fact sufficient to remove ring 22, to unscrew sleeve 20 so as to separate it from the threaded part 7 of the inner tube, and to remove this latter from the outer tube by pulling it from the front end of this latter. In order to reassemble the forceps, it is of course sufficient to carry out the same operations, but in the reverse order.

The operation of the forceps of the present invention is very simple. In order to close the jaws, the operator pivots arm 14 in the direction of arrow G about pin 15. While arm 14 pivots, its stud 18 pushes socket 19 and sleeve 20 rearwards, in the direction of arrow F. Since the inner tube 2 is integral with the sleeve, it moves in its turn in the direction of arrow F. Meanwhile, the swellings 11 of jaws 3 slide against the internal surface of the outer tube 1, which forces them to retract into the notches 12 and so allows the bent parts 10 to come together along the longitudinal axis of the two tubes.

In order to open jaws 3, it is sufficient to pivot arm 14 in the opposite direction. As this latter pivots about pin 15, the inner tube moves forwards while the jaws move away from each other under the effect of their elasticity, their swellings 11 projecting outside notches 12 and thus allowing them to move away from each other.

We claim:

1. Biopsy forceps for use with a contact endoscope having a body terminating in a distal end, said forceps comprising a hollow outer tube open at both ends, a hollow inner tube located coaxially within the outer tube, said inner tube being open at its rear end and terminating at its front end in at least one pair of diametrically opposed tongues that extend outwardly beyond the front end of the outer tube and in a direction substantially parallel to the longitudinal axis of the tubes and then bend inwardly at their far end at right angles to the longitudinal axis terminating in a series of teeth to form forceps jaws, the jaws being biased in a direction away from the axis, whereby movement of the tubes in one direction relative to one another causes the tongues of the jaws to slide into the outer tube and the forceps jaws to close and movement in the opposite direction causes the jaws to open, and control means for axially moving one of the tubes relative to the other to activate the jaws, whereby the endoscope can be inserted all the way through the forceps so that the distal end of the endoscope lies against the forceps jaws.

2. The forceps of claim 1, indicating one pair of tongues terminating in a single pair of forceps jaws.

3. The forceps of claim 1, wherein each tongue includes, between the point where it bends inwardly and where it joins the inner tube, a swelling cooperating with a longitudinal notch on the front end of the outer tube, the swelling resting in the notch and lying beneath the outer surface of the outer tube when the jaws are closed.

4. The forceps of claim 3 wherein the control means is interconnected with the inner tube to move the inner tube axially within the outer tube.

* * * * *